(12) United States Patent
Dhyllon

(10) Patent No.: US 10,434,087 B1
(45) Date of Patent: Oct. 8, 2019

(54) DIETARY SUPPLEMENT FORMULATIONS

(71) Applicant: Amen Dhyllon, Wynnewood, PA (US)

(72) Inventor: Amen Dhyllon, Wynnewood, PA (US)

(73) Assignee: SERENDIPITY TECHNOLOGIES LLC., Wynnewood, PA (US)

( * ) Notice: Subject to any disclaimer, the term of this patent is extended or adjusted under 35 U.S.C. 154(b) by 0 days.

(21) Appl. No.: 16/385,165

(22) Filed: Apr. 16, 2019

Related U.S. Application Data

(60) Provisional application No. 62/658,469, filed on Apr. 16, 2018.

(51) Int. Cl.

| | |
|---|---|
| *A61K 36/82* | (2006.01) |
| *A61K 33/00* | (2006.01) |
| *A61K 31/352* | (2006.01) |
| *A61K 31/355* | (2006.01) |
| *A61K 31/375* | (2006.01) |
| *A61K 31/714* | (2006.01) |
| *A61K 31/675* | (2006.01) |
| *A61K 31/12* | (2006.01) |
| *A61K 31/122* | (2006.01) |
| *A61K 36/33* | (2006.01) |
| *A61K 36/38* | (2006.01) |
| *A61K 36/73* | (2006.01) |
| *A61K 36/889* | (2006.01) |
| *A61K 31/4188* | (2006.01) |
| *A61K 31/047* | (2006.01) |
| *A61K 31/575* | (2006.01) |
| *A61K 36/53* | (2006.01) |
| *A61K 31/197* | (2006.01) |
| *A61K 36/81* | (2006.01) |
| *A61K 31/385* | (2006.01) |
| *A61K 36/484* | (2006.01) |
| *A61K 36/906* | (2006.01) |
| *A61K 36/63* | (2006.01) |
| *A61K 36/74* | (2006.01) |

(52) U.S. Cl.
CPC ........ *A61K 31/4188* (2013.01); *A61K 31/047* (2013.01); *A61K 31/12* (2013.01); *A61K 31/122* (2013.01); *A61K 31/197* (2013.01); *A61K 31/352* (2013.01); *A61K 31/355* (2013.01); *A61K 31/375* (2013.01); *A61K 31/385* (2013.01); *A61K 31/575* (2013.01); *A61K 31/675* (2013.01); *A61K 31/714* (2013.01); *A61K 33/00* (2013.01); *A61K 36/33* (2013.01); *A61K 36/38* (2013.01); *A61K 36/484* (2013.01); *A61K 36/53* (2013.01); *A61K 36/63* (2013.01); *A61K 36/73* (2013.01); *A61K 36/74* (2013.01); *A61K 36/81* (2013.01); *A61K 36/82* (2013.01); *A61K 36/889* (2013.01); *A61K 36/906* (2013.01)

(58) Field of Classification Search
None
See application file for complete search history.

(56) References Cited

U.S. PATENT DOCUMENTS

2012/0052137 A1\* 3/2012 Shirazi .................. A61K 36/45
424/729

\* cited by examiner

*Primary Examiner* — Robert A Wax
*Assistant Examiner* — William Craigo
(74) *Attorney, Agent, or Firm* — Adam Warwick Bell; Matthew Rupert Kaser

(57) ABSTRACT

Dietary supplement compositions directed to men and women and to the maintenance and improvement of human physiology, including weight, skin, hair, and general organ function and sexual health.

3 Claims, No Drawings

DIETARY SUPPLEMENT FORMULATIONS

RELATIONSHIP TO PRIOR APPLICATIONS

This non-provisional application claims priority to U.S. Provisional Patent Application Ser. No. 62/658,469 entitled "DIETARY SUPPLEMENT FORMULATIONS", filed 16 Apr. 2018, which is herein incorporated by reference in its entirety for all purposes. The present application claims priority to and the benefit of the above application 62/658,469.

FIELD OF THE INVENTION

The embodiments of the present invention relate to supplement compositions, and more particularly, the embodiments of the present invention relate to a dietary supplement compositions.

DESCRIPTION OF THE PRIOR ART

The basic force and condition behind all activities of human life is the presence of energy. Energy is the vital principle needed to sustain life and it is required for every aspect of existence—every act uses energy—thinking, feeling, walking, eating, drinking, dreaming, breathing etc. Energy is felt and experienced upon its expenditure. The energy we experience immediately after eating (such as sweets), or the hype we get following the consumption of coffee is from the expenditure of energy from body's energy reserves, not through its accumulation. Age, fatigue and stress make people feel deficient in energy. This drag in energy very often compromises body's mental alertness. The efficiency at work place and in personal management can be enhanced by addressing body's energy demands properly.

Dietary supplements are used by physically active people or weak people to increase their physical performance, physical fitness, improve their health, or reduce the potentially negative consequences of physical activity such as injury and chronic fatigue, or suppressed immune function.

A proper diet is a contributing factor in maintaining a healthy physiology, including healthy weight, skin, hair, and general organ function and sexual health. Men and women vary in their physiologies and to some degree benefit from different dietary supplement compositions.

Dietary supplement compositions are well known. There are a variety of known dietary supplement compositions that can affect human health, See the International Cosmetic Ingredient Dictionary and Handbook, 2004; and U.S. Pharmacopoeia Dietary Supplement Monographs; also, the NIH Office of Dietary Supplements online publication: https://ods.od.nih.gov/HealthInformation/dictionary.aspx, and the NIH fact sheet: https://ods.od.nih.gov/factsheets/list-all/.

Numerous innovations for dietary supplement compositions have been provided in the prior art and are incorporated herein by reference. For example:

U.S. Pat. No. 6,149,933 to Nelson "Dietary supplement for promotion of healthy hair and pigment restoration" which discloses a dietary supplement which is useful for the promotion of healthy hair containing copper salts, para-aminobenzoic acid, pantothenic acid and vitamin B6.

U.S. Pat. No. 6,630,158 to Popp et al "Dietary supplement composition and method for improving and maintaining healthy skin".

U.S. Pat. No. 9,028,890 to Ferrari et al. "Composition for improving sexual wellness".

U.S. Pat. No. 8,968,791 to Moore et al. "Dietary supplements for promotion of growth, repair, and maintenance of bone and joints".

U.S. Pat. No. 9,808,441 issued to Hornack et al. which teaches a dietary and/or therapeutic supplement composition including a quantity of a dietary and/or therapeutic supplement agent comprising an alkaline electrolyte additive to increase absorbtion of components.

U.S. Pat. No. 9,744,182 issued to Daniels et al. which discloses various manufactured dietary supplements that contain a phospholipid extract, folic acid, vitamin D, vitamin $B_6$, vitamin $B_{12}$, Vitamin E, Vitamin C, iodine, iron, and magnesium. The manufactured dietary supplements further contain a phospholipid extract that contains phospholipid-DHA.

U.S. Pat. No. 9,907,825 issued to Gokaraju et al. that discloses synergistic dietary supplement compositions including at least two ingredients selected from the extracts and fractions derived from *Sphaeranthus indicus, Coleus aromaticus, Cissus quadrangularis, Curcuma longa, Garcinia mangostana, Citrullus lanatus, Ocimum sanctum, Trachyspermum ammi* and *Cinnamomum tamala* as a natural energy enhancer for enhancing physical performance, muscle strength, muscle mass, mental alertness, and energy levels in a mammal.

There exists a need for effective and reliable dietary supplement compositions directed to men and women and to the maintenance and improvement of human physiology, including weight, skin, hair, and general organ function and sexual health.

SUMMARY OF THE INVENTION

The invention provides a dietary supplement composition, which avoids the disadvantages of the prior art and which is directed to the maintenance and improvement of human physiology, including weight, skin, hair, and general organ function and sexual health.

The dietary supplemental compositions of the present invention include compositions providing combinations and formulations of different amounts depending upon the user's choice, and also may contain non-active ingredients, such as, drug carriers, drug fillers, and drug absorption enhancers. Flavorings such as sweeteners may also be added the to the compositions of the invention.

Furthermore, the dietary supplemental compositions of the present invention may be oral, and are formulated in different strengths as exemplified in the various embodiments discussed.

One object of the present invention is to provide effective and reliable dietary supplement compositions directed to men and women and to the maintenance and improvement of human physiology, including weight, skin, hair, and general organ function and sexual health. A first embodiment of the dietary supplement compositions improves one's hair. A second embodiment of the dietary supplement compositions improves women's health. A third embodiment of the dietary supplement compositions improves one's teeth. A fourth embodiment of the dietary supplement compositions improves one's weight. A fifth embodiment of the dietary supplement compositions improves men's health. And, a sixth embodiment of the dietary supplement compositions improves one's joints. The 6 embodiments contain various ingredients and various amounts of the ingredients.

DETAILED DESCRIPTION

The invention encompasses effective and reliable dietary supplement compositions directed to men and women and to the maintenance and improvement of human physiology, including weight, skin, hair, and general organ function and sexual health. A first embodiment of the dietary supplement compositions improves one's hair. A second embodiment of the dietary supplement compositions improves women's health. A third embodiment of the dietary supplement compositions improves one's teeth. A fourth embodiment of the dietary supplement compositions improves one's weight. A fifth embodiment of the dietary supplement compositions improves men's health. And, a sixth embodiment of the dietary supplement compositions improves one's joints.

Each of the six embodiments is broken down into three examples, infra. The first example is a list of the ingredients with no set quantities. However, it will be clear that any quantities provided will be those that are practical and consistent with customary human consumption. The second example is the ranges of the quantities of the ingredients with a 20%+/− variation, i.e., with a variance of 20% more or less of each ingredient. In other embodiments, the variation may be plus or minus 5%, 10%, 15%, 25%, 30%, 35%, 40%, 50%, 60% or 75% by weight. Indeed, in certain embodiments, the amount of any particular ingredient may be several times that shown, for example twice, three times, 5 times or ten times that shown in the examples. The third example is the optimum quantities of the ingredients. Other non-enumerated ingredients may also be present. Note that in alternative embodiments the invention may encompass a formulation consisting essentially of a combination of any of the listed active components, but not including any other active components. These formulations may include non-active ingredients such as fillers and carriers, flavor enhancers, sweeteners, etc.

FIRST EMBODIMENT—ULTIMATE RICH HAIR

Example 1a—Ingredients

Biotin
Saw Palmetto Extract (DHT Blocker)
Vitamin E
Vitamin C
Inositol
Brahami
Nirgundi
Vitamin B12
Beta sitosterol
Rosemary Extract
Vitamin B6

Example 1b—Ranges of Quantities of Ingredients

Biotin: 10 mg±2 mg
Saw Palmetto Extract (DHT Blocker): 60 mg±12 mg
Vitamin E: 75 IU±15 IU
Vitamin C: 100 mg±20 mg
Inositol: 100 mg±20 mg
Brahami: 100 mg±20 mg
Nirgundi: 0.20 mg±0.04 mg
Vitamin B12: 0.50 mg±0.1 mg
Beta sitosterol: 1.5 mg±0.03 mg
Rosemary Extract: 2.5 mg±0.5 mg
Vitamin B6: 50 mg±10 mg

Example 1c—Optimum Quantities of Ingredients

Biotin: 10 mg
Saw Palmetto Extract (DHT Blocker): 60 mg
Vitamin E: 75 IU
Vitamin C: 100 mg
Inositol: 100 mg
Brahami: 100 mg
Nirgundi: 0.20 mg
Vitamin B12: 0.50 mg
Beta sitosterol: 1.5 mg
Rosemary Extract: 2.5 mg
Vitamin B6: 50 mg

SECOND EMBODIMENT—ULTRA WOMEN

Example 2a—Ingredients

Valerian Extract
Soy isoflavinoids
Saffron Extract
Fenugreek Extract
Apple cider Extract
Calcium citrate maleate
Melatonin
Resveratrol
Grape seed Extract
Vitamin C
Vitamin B12
Vitamin B6

Example 2b—Ranges of Quantities of Ingredients

Valerian Extract: 100 mg±20 mg
Soy isoflavinoids: 50 mg±10 mg
Saffron Extract: 10 mg±2 mg
Fenugreek Extract: 100 mg±20 mg
Apple cider Extract: 100 mg±20 mg
Calcium citrate maleate: 50 mg±10 mg
Melatonin: 2 mg±0.4 mg
Resveratrol: 20 mg 4 mg
Grape seed Extract: 50 mg±10 mg
Vitamin C: 100 mg±20 mg
Vitamin B12: 0.30 mg±0.06 mg
Vitamin B6: 25 mg±5 mg

Example 2c—Optimum Quantities of Ingredients

Valerian Extract: 100 mg
Soy isoflavinoids: 50 mg
Saffron Extract: 10 mg
Fenugreek Extract: 100 mg
Apple cider Extract: 100 mg
Calcium citrate maleate: 50 mg
Melatonin: 2 mg
Resveratrol: 20 mg
Grape seed Extract: 50 mg
Vitamin C: 100 mg
Vitamin B12: 0.30 mg
Vitamin B6: 25 mg

THIRD EMBODIMENT—TEETH ULTRA WHITE

Example 3a—Ingredients

Glutathione
Ashwagandha (Indian *Ginseng*)
Alpha Lipoic acid
Licorice
Banana leaf Extract
Olive leaf extract
Curcumin
CoQ10
Vitamin E
Vitamin C
Vitamin B12
Vitamin B6

Example 3b—Range of Quantities of Ingredients

Glutathione: 50 mg±20 mg
Ashwagandha: 100 mg±20 mg
Alpha Lipoic acid: 50 mg±10 mg
Licorice: 50 mg±10 mg
Banana leaf Extract: 60 mg±12 mg
Olive leaf extract: 50 mg±20 mg
Curcumin: 50 mg±20 mg
CoQ10: 25 mg±5 mg
Vitamin E: 75 mg±15 mg
Vitamin C: 100 mg±20 mg
Vitamin B12: 0.50 mg±0.1 mg
Vitamin B6: 50 mg±10 mg

Example 3c—Optimum Quantities of Ingredients

Glutathione: 50 mg
Ashwagandha: 100 mg
Alpha Lipoic acid: 50 mg
Licorice: 50 mg
Banana leaf Extract: 60 mg
Olive leaf extract: 50 mg
Curcumin: 50 mg
CoQ10: 25 mg
Vitamin E: 75 mg
Vitamin C: 100 mg
Vitamin B12: 0.50 mg
Vitamin B6: 50 mg

FOURTH EMBODIMENT—ULTRA SLIM

Example 4a—Ingredients

Nopal Extract
Green Coffee
*Garcinia*
Green Tea
Raspberry Ketones
Apple cider vinegar
Triphala
Vanadium
Chromium
Vitamin E
Vitamin C
Vitamin B12
Forskolin
Vitamin B6

Example 4b—Range of Quantities of Ingredients

Nopal Extract: 100 mg±20 mg
Green Coffee: 100 mg±20 mg
*Garcinia:* 100 mg±20 mg
Green Tea: 100 mg±20 mg
Raspberry Ketones: 75 mg±15 mg
Apple cider vinegar: 75 mg±15 mg
Triphala: 50 mg±10 mg
Vanadium: 2 mg±0.4 mg
Chromium: 0.10 mg±0.012 mg
Vitamin E: 25 mg±5 mg
Vitamin C: 50 mg±10 mg
Vitamin B12: 0.50 mg±0.1 mg
Forskolin: 5 mg±1 mg
Vitamin B6: 25 mg±5 mg

Example 4c—Optimum Quantities of Ingredients

Nopal Extract: 100 mg
Green Coffee: 100 mg
*Garcinia:* 100 mg
Green Tea: 100 mg
Raspberry Ketones: 75 mg
Apple cider vinegar: 75 mg
Triphala: 50 mg
Vanadium: 2 mg
Chromium: 0.10 mg
Vitamin E: 25 mg
Vitamin C: 50 mg
Vitamin B12: 0.50 mg
Forskolin: 5 mg
Vitamin B6: 25 mg

FIFTH EMBODIMENT—ULTRA MEN

Example 5a—Ingredients

Olive leaf extract
Horny goat weed
Maca Root Extract
Saw Palmetto
Pumpkin seed extract
*Rhodiola Rosea*
*Ginseng*
Beta silosterol
Apple cider Extract
Vitamin C
Vitamin B12
Vitamin B6

Example 5b—Ranges of Quantities of Ingredients

Olive leaf extract: 100 mg±20 mg
Horny goat weed: 50 mg±10 mg
Maca Root Extract: 25 mg±5 mg
Saw Palmetto: 60 mg±12 mg
Pumpkin seed extract: 50 mg±10 mg
*Rhodiola Rosea:* 50 mg±10 mg
*Ginseng:* 50 mg±10 mg
Beta silosterol: 25 mg±5 mg
Apple cider Extract: 50 mg±10 mg
Vitamin C: 100 mg±20 mg
Vitamin B12: 0.50 mg±0.1 mg
Vitamin B6: 50 mg±10 mg Example 5c—Optimum Quantities of Ingredients Olive leaf extract: 100 mg
Horny goat weed: 50 mg
Maca Root Extract: 25 mg
Saw Palmetto: 60 mg
Pumpkin seed extract: 50 mg
*Rhodiola Rosea:* 50 mg
*Ginseng:* 50 mg
Beta silosterol: 25 mg
Apple cider Extract: 50 mg
Vitamin C: 100 mg
Vitamin B12: 0.50 mg
Vitamin B6: 50 mg

SIXTH EMBODIMENT—ULTIMATE JOINTS

Example 6a—Ingredients

Olive leaf extract
Calcium Citrate Maleate
Vitamin K
Saw Palmetto
Pumpkin seed extract
Vitamin C
Green Lipid mussel
Vitamin B12
Chondritin sulphate
*Boswellia*

Example 6b—Ranges of Quantities of Ingredients

Olive leaf extract: 100 mg±20 mg
Calcium Citrate Maleate: 250 mg±25 mg
Vitamin K: 0.25 mg±0.5 mg
Saw Palmetto: 50 mg±10 mg
Pumpkin seed extract: 25 mg±5 mg
Vitamin C: 100 mg±20 mg
Green Lipid mussel: 50 mg±10 mg
Vitamin B12: 0.5 mg±0.1 mg
Chondritin sulphate: 50 mg±10 mg
*Boswellia:* 50 mg±10 mg Example 6c—Optimum Quantities of Ingredients Olive leaf extract: 100 mg
Calcium Citrate Maleate: 250 mg
Vitamin K: 0.25 mg
Saw Palmetto: 50 mg
Pumpkin seed extract: 25 mg
Vitamin C: 100 mg
Green Lipid mussel: 50 mg
Vitamin B12: 0.5 mg
Chondritin sulphate: 50 mg
*Boswellia:* 50 mg

GENERAL DISCLOSURES AND DEFINITIONS

In this disclosure, vitamin K may be, in various embodiments, vitamin K2 or vitamin K2 (MK-7), or any other variation of vitamin K.

The above components may be present as variants or salts thereof or may be compounded with various other components. They may be present in solid, powder or liquid form.

The disclosed formulations may be formulated as oral formulations and can be prepared in the form of powder, granules, capsules with a pharmaceutically acceptable carrier, a forming agent, a diluent and the like. Further, the level of component administration can vary according to rate of body absorption, body weight, age, sex and health state of a patient, diet, time and method of administration, excretion rate, and the like.

Apple cider extract refers to apple cider vinegar which is the product of fermenting crushed apples.

Nopal extract is an extract from the Nopal cactus (prickly pear). See Arch Invest Med (Mex). 1989 July-September; 20(3):211-6; Effect of a dehydrated extract of nopal (*Opuntia ficus indica* Mill.) on blood glucose.

Brahami is derived from *Bacopa monnieri*. *Bacopa* has a long history of use and is believed to enhance memory and cognition. It is a very important herb in Ayurveda where it is considered a 'Rasayana' See 10.1002/9781118543436.ch16: Phytopharmacy: An Evidence-Based Guide to Herbal Medical Products, pp. 69-71.

Nirgundi is a herb used in traditional medicine: see World Journal of Pharmaceutical Sciences ISSN (Print): 2321-3310; ISSN (Online): 2321-3086 and https://www.researchgate.net/publication/318283200_Nirgundi_Vitex_negundo.

β-Sitosterol is one of several phytosterols with chemical structures similar to that of cholesterol. Sitosterols are white, waxy powders with a characteristic odor. They are hydrophobic and soluble in alcohols. β-sitosterol is being studied for its potential to reduce benign prostatic hyperplasia (BPH) and blood cholesterol levels.

Ashwagandha is a plant. The root and berry are used to make medicine. Ashwagandha is used for arthritis, anxiety, bipolar disorder, attention deficit hyperactivity disorder (ADHD), balance, obsessive-compulsive dirorder (OCD), trouble sleeping (insomnia), tumors, tuberculosis, asthma, a skin condition marked by white patchiness (leukoderma), bronchitis, backache, fibromyalgia, menstrual problems, hiccups, Parkinson's disease, and chronic liver disease. It is also used to reduce side effects of medications used to treat cancer and schizophrenia. Ashwagandha is used to reduce levels of fat and sugar in the blood. Ashwagandha is also used as an "adaptogen" to help the body cope with daily stress, and as a general tonic.

Banana leaf extract contains compounds which may be anti-diabetic in nature.

*Garcinia* is a small tree that grows in India and Southeast Asia. The fruit rind contains the chemical hydroxycitric acid (HCA) and is used to make medicine. It contains the chemical hydroxycitric acid (HCA). Some laboratory research suggests that HCA might prevent fat storage, control appetite, and increase exercise endurance.

Triphala is an Ayurvedic herbal rasayana formula consisting of equal parts of three myrobalans, taken without seed: Amalaki (*Emblica officinalis*), Bibhitaki (*Terminalia bellirica*), and Haritaki (*Terminalia chebula*). See Ayurvedic pharmacopoeia committee. The Ayurvedic Formulary of India, Part I, 2nd English ed. New Delhi: Controller of Publications; 2003.

Forskolin (coleonol) is a labdane diterpene that is produced by the Indian *Coleus* plant (*Plectranthus barbatus*). Other names include pashanabhedi, Indian *coleus*, makandi, HL-362, mao hou qiao rui hua. As with other members of the large diterpene family of natural products, forskolin is derived from geranylgeranyl pyrophosphate (GGPP). Forskolin contains some unique functional elements, including the presence of a tetrahydropyran-derived heterocyclic ring. Forskolin is a commonly used material in laboratory research to increase levels of cyclic AMP by stimulation of adenylate cyclase.

*Rhodiola rosea* (commonly golden root, rose root, roseroot, Aaron's rod, Arctic root, king's crown, lignum rhodium, orpin rose) is a perennial flowering plant in the family Crassulaceae. It grows naturally in wild Arctic regions of Europe (including Britain), Asia, and North America, and can be propagated as a groundcover. *Rhodiola rosea* has been used in traditional medicine for several disorders, notably including treatment of anxiety and depression. As of 2019, there is no high-quality clinical research to indicate it is effective for treating any disorder, and the United States Food and Drug Administration has issued several warnings to manufacturers of *R. rosea* dietary supplements for making false health claims about its safety and efficacy.

Additional ingredients included in the dietary supplemental compositions may be active ingredients such as vitamins or herbal extracts, or may be non-active ingredients, including carriers, fillers, absorption enhancers, flavors, stabilizers, sweetening agents etc.

While the embodiments of the present invention have been illustrated and described as embodied in dietary supplement compositions, nevertheless, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

All references and publications referred to herein are incorporated by reference for all purposes.

The invention claimed is:

1. A dietary supplement composition for slimming, comprising:
   a) Nopal Extract;
   b) Green Coffee:
   c) *Garcinia;*
   d) Green Tea;
   e) Raspberry Ketones;
   f) Apple cider vinegar;
   g) Triphala;
   h) Vanadium;
   i) Chromium;
   k) Vitamin E;
   l) Vitamin C;
   m) Vitamin B12;
   o) Forskolin; and
   p) Vitamin B6.

2. The composition of claim 1, wherein the amounts of components are as follows:
   a) said Nopal Extract is 100 mg±20 mg;
   b) said Green Coffee is 100 mg±20 mg;
   c) said *Garcinia* is 100 mg±20 mg;
   d) said Green Tea is 100 mg±20 mg;
   e) said Raspberry Ketones is 75 mg±15 mg;
   f) said Apple cider vinegar is 75 mg±15 mg;
   g) said Triphala is 50 mg±10 mg;
   h) said Vanadium is 2 mg±0.4 mg;
   i) said Chromium is 0.10 mg±0.04 mg;
   j) said Vitamin E is 25 mg±5 mg;
   k) said Vitamin C is 50 mg±10 mg;
   l) said Vitamin B12 is 0.50 mg±0.10 mg;
   m) said Forskolin is 5 mg±1 mg; and
   n) said Vitamin B6 is 25 mg±5 mg.

3. The composition of claim 1, wherein the amounts of components are as follows:
   a) said Nopal Extract is 100 mg;
   b) said Green Coffee is 100 mg;
   c) said *Garcinia* is 100 mg;
   d) said Green Tea is 100 mg;
   e) said Raspberry Ketones is 75 mg;
   f) said Apple cider vinegar is 75 mg;
   g) Triphala is 50 mg;
   h) said Vanadium is 2 mg;
   i) said Chromium is 0.10 mg;
   j) said Vitamin E is 25 mg;
   k) said Vitamin C is 50 mg;
   l) said Vitamin B12 is 0.50 mg;
   m) said Forskolin is 5 mg;
   n) said Vitamin B6 is 25 mg.

\* \* \* \* \*